United States Patent [19]

Hegemann et al.

[11] Patent Number: 4,860,738
[45] Date of Patent: Aug. 29, 1989

[54] HAND HELD METERED SPRAY DISPENSER

[75] Inventors: Manfred K. Hegemann, South Nyack, N.Y.; Edward J. Drozd, Jr., Lake Hiawatha, N.J.

[73] Assignee: Schering Corporation, Kenilworth, N.J.

[21] Appl. No.: 212,847

[22] Filed: Jun. 29, 1988

Related U.S. Application Data

[62] Division of Ser. No. 451,311, Dec. 20, 1982, Pat. No. 4,771,769.

[51] Int. Cl.⁴ ............................................. A61M 11/00
[52] U.S. Cl. ................................. 128/200.22; 222/162
[58] Field of Search ...................... 128/200.23, 200.22, 128/203.15, 203.22, 203.23, 203.28, 200.14; 604/37, 38, 214, 212; 222/207, 162–164, 160, 211, 321

[56] References Cited

U.S. PATENT DOCUMENTS

| | | | |
|---|---|---|---|
| 1,738,961 | 12/1929 | Neeb . | |
| 2,434,875 | 1/1948 | Turnbull | 128/250 |
| 2,673,008 | 3/1954 | Ryan | 222/162 |
| 2,796,294 | 6/1957 | McKinnon | 299/88 |
| 2,904,223 | 9/1959 | Ryan | 222/162 |
| 2,914,222 | 11/1959 | Meshberg | 222/162 |
| 3,152,734 | 10/1964 | Berry | 222/211 |
| 3,302,834 | 2/1967 | Alsop | 222/162 |
| 3,303,847 | 2/1967 | Eaton | 128/232 |
| 3,381,860 | 5/1968 | Armour | 222/211 |
| 3,405,843 | 10/1968 | Watson | 222/95 |
| 3,406,909 | 10/1968 | Pfeiffer | 239/333 |
| 3,716,170 | 2/1973 | Mangels | 222/162 |
| 3,818,908 | 5/1974 | Phillips | 128/173 |
| 3,820,698 | 6/1974 | Franz | 222/205 |
| 3,871,557 | 3/1975 | Smrt | 222/162 |
| 3,900,138 | 8/1975 | Phillips | 222/340 |
| 3,949,939 | 4/1976 | Brown | 239/350 |
| 4,061,247 | 12/1977 | Meshberg | 222/1 |
| 4,077,548 | 3/1978 | Beard | 222/321 |
| 4,082,222 | 4/1978 | Boris | 239/331 |
| 4,088,425 | 5/1978 | Bennett | 417/444 |
| 4,089,442 | 5/1978 | Hafele et al. | 222/321 |
| 4,114,811 | 9/1978 | Loeffler | 239/288.5 |
| 4,168,032 | 9/1979 | Sneider | 239/327 |
| 4,771,769 | 9/1988 | Hegemann et al. | 222/162 |

FOREIGN PATENT DOCUMENTS

| | | |
|---|---|---|
| 0092359 | 10/1983 | European Pat. Off. . |
| 2312421 | 12/1976 | France . |
| 1517642 | 7/1978 | United Kingdom . |
| 1530333 | 10/1978 | United Kingdom . |

Primary Examiner—Max Hindenburg
Assistant Examiner—K. M. Reiche
Attorney, Agent, or Firm—Warrick E. Lee, Jr.

[57] ABSTRACT

A hand held metered spray dispenser including a housing, a nozzle on the housing, a fluid container in the housing, an orifice in the housing, and a converter pivotal to the housing for converting a manual force applied through the orifice along a manual force axis to a force moving the container along a pumping axis transverse to the manual force axis to dispense a metered amount of fluid through the nozzle along a dispensing axis substantially coincidental with the pumping axis.

13 Claims, 2 Drawing Sheets

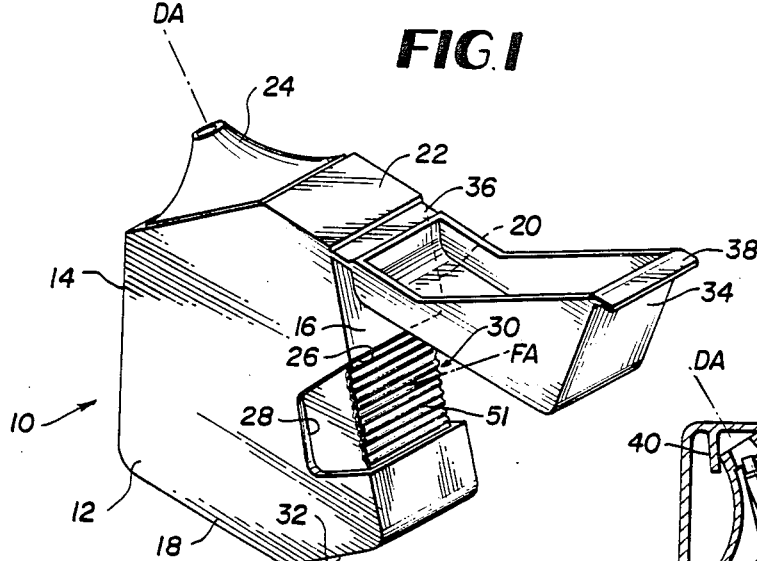
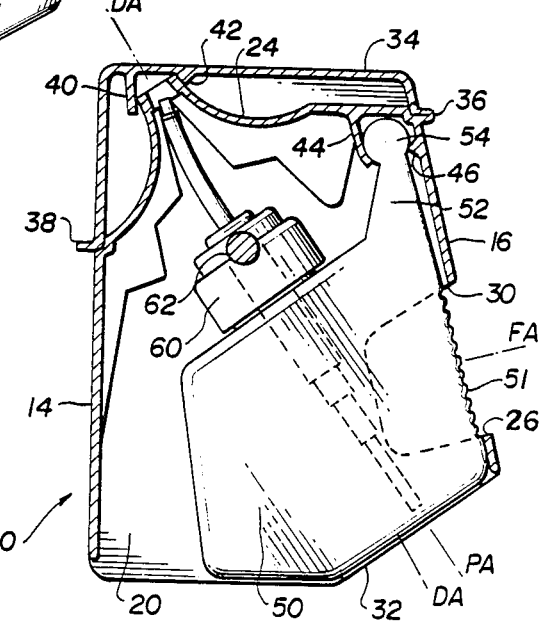
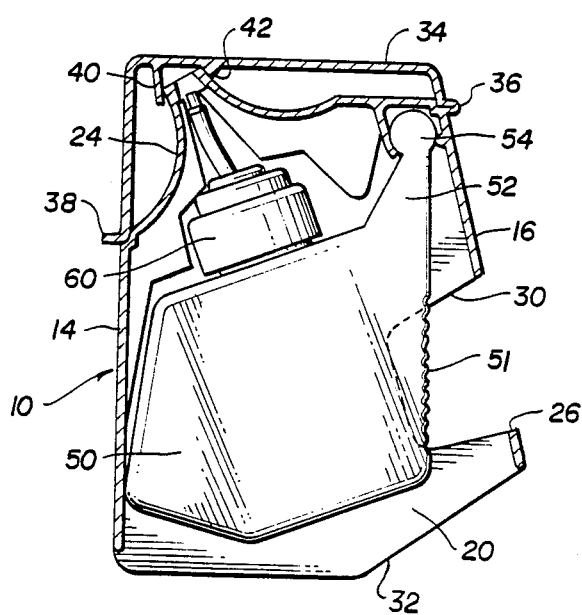
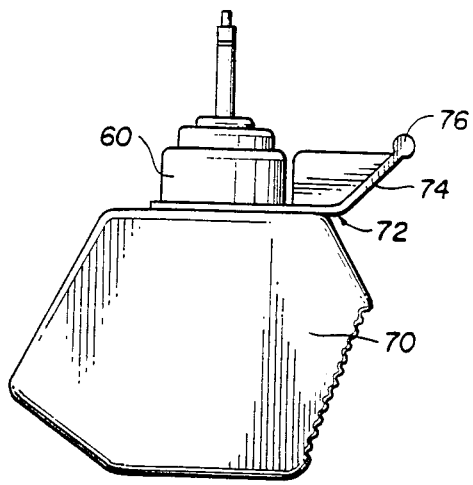
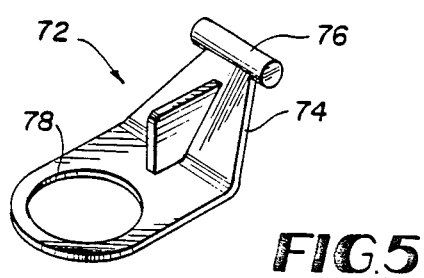

HAND HELD METERED SPRAY DISPENSER

This is a division of application Ser. No. 451,311 filed Dec. 20, 1982 now U.S. Pat. No. 4,771,769

BACKGROUND OF THE INVENTION

The present invention relates generally to spray dispensers and, more specifically, to an improved hand held spray dispenser of pharmaceuticals.

The dispensing of pharmaceuticals into a body cavity, for example, a nostril, has generally included a squeeze bottle having a nozzle which is inserted into the nostril cavity. The amount of fluid dispensed with each squeeze of the bottle is dependent on how the person squeezes it. Thus, one cannot be assured of reproducably accurate delivery. Since dosage consistency is important in treating a medical condition, a pump which meters the drug amount is needed. A typical example of prior art metering pumps are U.S. Pat. Nos. 2,434,875 to Turnbull et al; U.S. Pat. No. 3,820,698 to Franz; U.S. Pat. No. 3,949,939 to Brown and United Kingdom Patent Specification No. 1,517,642 to Syntex.

In each of the above devices, which are merely examples, the metering pump reciprocates along an axis coincident with the nozzle dispensing axis to pump metered portions of liquid from the container through the nozzle. The forces applied by the user are along the axis of pumping and dispensing. The user grasps the dispenser between his thumb and the remainder of his fingers and contracts. Generally what happens is that the nozzle is removed from the target area during dispensing by the force and action required to operate the pump. This is both inconvenient and undesirable since the product does not reach the intended site and often splashes the face.

Other types of atomizers or manual metered spray pumps have applied the force along the axis of reciprocation of the pump and dispense liquid along an axis transverse to the pumping actions. These generally include a deflector or other device at the output of the pump to redirect the fluid. Typical examples are U.S. Pat. No. 3,900,138 to Phillips; U.S. Pat. No. 4,082,222 to Boris; U.S. Pat. No. 4,088,425 to Bennett; and U.S. Pat. No. 4,089,442 to Hafele et al. Even though these patents specifically show the axis upon which the manual force is applied as being traversed to the axis of dispensing, the force is applied along the axis of the pump.

Another alternative is to use a trigger mechanism which receives a manual force transerse to the pumping axis and to dispense the fluid through a nozzle which is transverse to the dispensing axis. This is illustrated in U.S. Pat. No. 4,077,548 to Beard. The trigger and adapter are positioned on the top of the dispensing bottle and manually actuate the pump by pivoting about a hinge point. As discussed in Beard, this method minimizes the lateral component of the saddle member on the pushbutton of the pump. Although the trigger mechanism of Beard may be an improvement over the prior art, it is clumsy and is generally not acceptable for use in small dose applicators of pharmaceuticals, for example, nasal sprays. Since the trigger extends substantially away from the body, the dispenser can be accidentally actuated if carried in the user's purse or pocket. Thus, this configuration is not practical for a pharmaceutical which must be available to the user several times a day.

SUMMARY OF THE INVENTION

An object of the present invention is to provide a improved hand held manual meter pump.

Another object of the present invention is to provide a hand held manual metered spray dispenser wherein actuation of the pump does not produce undesirable motion of the nozzle.

Still another object of the present invention is to provide an improved hand held metered spray dispenser which allows accurate postioning of the nozzle to minimize fluid losses.

Still an even further object of the present invention is to provide a compact hand held metered spray dispenser requiring minimum manual actuation forces.

A still even further object of the present invention is to provide a readily and inexpensively manufactured hand held metered spray dispenser which accurately dispenses small amounts of fluids to precise locations.

An even further object of the present invention is to provide a compact hand held metering pump which minimizes the occurrence of accidental actuation.

These and other objects of the present invention are achieved by a metered spray dispenser having a housing with a nozzle at the top thereof, a container of fluid movably connected to the interior of the housing, a manual pump between the container and the nozzle whose axis is substantially coincident with the dispensing axis of the nozzle, an orifice in the side of the housing through which manual force is applied along a manual force axis transverse to the dispensing axis and a converter pivotally connected to the housing and engaging the container to convert a manual force applied through the orifice along the manual force axis to a force moving the container along the pumping axis activating the pump to dispense a metered amount of fluid through the nozzle.

In one embodiment, the converter is a hinge pivotally mounting the container in the housing with a portion of the container adjacent the orifice whereby the manual force is applied directly to the container. The surface of the container juxtaposed the orifice in the housing has a high coefficient of friction to prevent slipping of the fingers upon application of the pumping force. The housing, nozzle and a first hinge portion are a unitary molded structure. The container may include an integrally formed second hinge portion to cooperate with the first hinge portion to pivotally connect the container to the housing or a separate hinge portion may be used and secured to the container by the pump structure.

In another embodiment, the converter is an L-shaped cross-sectional structure pivotally connected to the housing with a first portion substantially following the contour of the housing across the orifice and a second portion interior the housing substantially orthogonal to the first portion and engaging the container. The converter and housing may be a unitary molded structure or separate structures.

Other objects, advantages and novel features of the present invention will become evident upon review of the detailed description of the preferred embodiments in conjunction with the accompanying drawings.

BRIEF DESCRIPTION OF THE DRAWINGS

FIG. 1 is a perspective view of a hand held metered spray dispenser with the cap open incorporating the principles of the present invention.

FIG. 2 is a side elevation of the metered spray dispenser of FIG. 1 with the cap closed and the side wall cutaway showing the fluid container and pump in its initial position.

FIG. 3 is the metered spray dispenser of FIG. 2 with the container and pump in its dispensed position.

FIG. 4 is a side elevation of a container with a separate and distinct hinge member.

FIG. 5 is a perspective view of the hinge member of FIG. 4.

DESCRIPTION OF THE PREFERRED EMBODIMENTS

Figure 6:
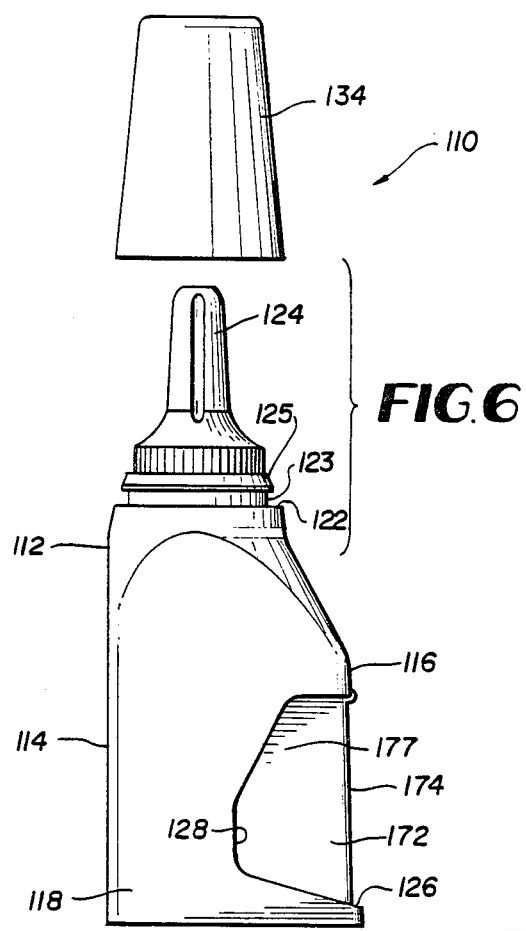
FIG. 6 is a side elevation of another embodiment of a hand held metered spray dispenser with the cap off incorporating the principles of the present invention.

A hand held metered spray dispenser 10 includes a housing, a container for fluid and a manually actuated pump to dispense fluid from the container through a nozzle on the housing. As specifically illustrated in FIG. 1, housing 12 includes a front wall 14, a back wall 16 and side walls 18 and 20. A top wall 22 includes a nozzle 24 having a dispensing axis DA. The nozzle 24 is tapered and has a generally conical shape for ease of insertion into a nostril or other body cavities. The back wall 16 includes an orifice 26, the side wall 18 includes an indenture 28 contiguous with the orifice 26 and the side wall 20 includes an indenture 30 contiguous with the orifice 26. The orifice 26 and indentures 28 and 30 form subtantially a slot and the orifice 26 has an axis FA through which the manual force is applied and which is substantially transverse to the dispensing axis DA. The bottom of the housing 12 is open at 32 to provide an avenue for loading and unloading the container.

A cap 34 is connected to the top wall 22 by a living hinge 36 The cap 34 includes a rim 38 which extends past the front wall 14 of the closed position as illustrated in FIG. 2 to aid in opening of the cap. As illustrated specifically in FIG. 2, interior the cap 34 are a pair of spaced longitudinal ribs 40 and 42 which engage the nozzle 24 when the cap is in the closed position and acts as a lock mechanism for the cap to prevent evaporation and spillage. Also as illustrated in FIG. 2 is a lip 44 extending down from the interior of the top wall 22 and a lip 46 on the back wall 16 to define a confined space therebetween. The lips 44 and 46 form what will constitute one portion of a hinged element to mount a container within the housing to rotate therein and convert manual force along axis FA to a force along the dispensing axis DA as will be described below.

As is evident from the drawing, the dispensing axis DA of the nozzle 24 is inclined relative to the front wall 14. The back will 16 is substantially parallel to the dispensing axis DA.

This specific configuration allows the nozzle 24 to be inserted within a nostril while still leaving room for the thumb to engage the front wall 14.

Preferably, the housing 12, the nozzle 24, the cap 34, living hinge 36 and the hinge elements 44 and 46 are a unitary molded structure. Although this is a optimum cost effective way of manufacturing, it should be noted that these may be separate and distinct pieces assembled into the final configuration. It should also be noted that although the dispenser is illustrated as being a box-shape, the front, back and sides may be a continuous surface in some continuous curve The importance being that the orifice 26 with the indentures 28 and 30 allows access to a substantial depth to the interior of the housing 12.

A container 50 for containing the liquid to be dispensed is substantially the shape of the housing 12 with the bottom edge matching the bottom of the housing 12. A portion 51 of the rear wall of the container 50 juxtaposed the orifice 26 in the housing has a high coefficient of friction. the high coefficient of friction may be provided by a plurality of grooves to prevent slipping of the finger which will apply the force directly to the container through the orifice 26 and indentures 28 and 30 of the housing. An extension 52 of the container terminates in a cylindrical section 54 which is received between the lips 44 and 46 of the housing to form the second portion of a hinge and to pivotally mount the container 50 to the interior of the housing 12. As with the housing, it is preferable that the container 50 and the extension 52 and hinge element 54 is formed as a unitary molded structure.

Connecting the interior of the container 50 to the nozzle 24 is a pump 60. The pump 60 includes a spring 62 which returns the compressed pump components to their extended position when the pumping force is removed. These pumps also generally include check valves, and accumulators or reservoirs such that a metered amount of fluid is drawn into the pump reservoir during a contracted to an extended portion of the cycle and this metered portion is dispensed during an extended to a contracted portion of the cycle. The specific details of the pump are well known and will not be discussed in detail. Any of the pumping structures of the patents discussed in the Background of the Invention may be used.

The dispenser 10 can be used, for example, to dispense expensive life-saving drugs, for example, interferon, in the nostrils Because of the expense, the pump must be very accurate and capable of dispensing small amounts per cycle. The fluid may be a colloid solution. The pump should be capable of dispensing metered amounts in the range of 0.02 to 0.2 milliliters and preferably in the range of 0.04 to 0.1 milliliters. The pump should have a reproducibility in the range of 50% to 100% and preferably in the range of 80% to 100%.

The spring 62 of the pump is used to maintain the container 50 in its initial position as illustrated in FIG. 2 and to return it from its pivoted position of FIG. 3 back to the position of FIG. 2 after the manual force is removed. As illustrated in FIG. 3, the pumping axis PA of the pump is coincident with the dispensing axis DA in the contracted position As illustrated in FIG. 2, the pumping axis PA is substantially coincident with the dispensing axis DA. As is well known, the meter pump 62 contracts and expands reciprocally along the pumping axis PA to dispense a metered amount of liquid as a spray.

In use, the cap 34 is removed exposing the nozzle 24 which is inserted into a body orifice. The housing is grasped in the hand with one finger on the ridge portion 51 of the container in the orifice 26 with the remainder of the fingers wrapped around the housing. Upon application of the force along the force axis FA transverse to the dispensing axis DA, directly onto the container 50, the container moves along pumping axis PA from the initial position of FIG. 2 to the position in FIG. 3. This rotation causes the portions of the pump to contact the interior of the housing and contract. This contraction dispenses a metered portion of liquid from the container 50 through the nozzle 24, with the pumping axis PA aligned with the dispensing axis DA. Upon release of the manual force, the spring 62 of the pump returns the container 50 to its initial position illustrated in FIG. 2.

As with the housing, the preferred embodiment for the container 50, the extension 52 and the hinge 54 is a unitary molded structure. Alternatively, as illustrated in FIGS. 4 and 5, the container 70 may be distinct and separate from the hinge element 72. The shape of the container 70 is substantially that of container 50, illustrated in FIG. 2, except for the extension 52 and the hinge element 54. The hinge 72 includes an extended portion 74 terminating in a cylindrical hinge element 76. An orifice 78 within the hinge member 72 is received on the neck of the container 70 and is held thereto by the pump 60 which is generally screwed onto the top of the container 70. Alternatively, the hinge can be attached to the bottom or other area of the container. The embodiment illustrated in FIG. 4 functions identical to that of the container 50 illustrated in FIGS. 2 and 3.

Figure 7:
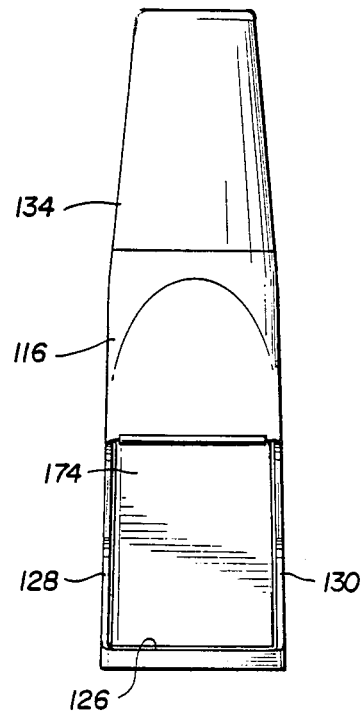
FIG. 7 is a back elevation of the embodiment of FIG. 6 with the cap on the housing.
Figure 8:
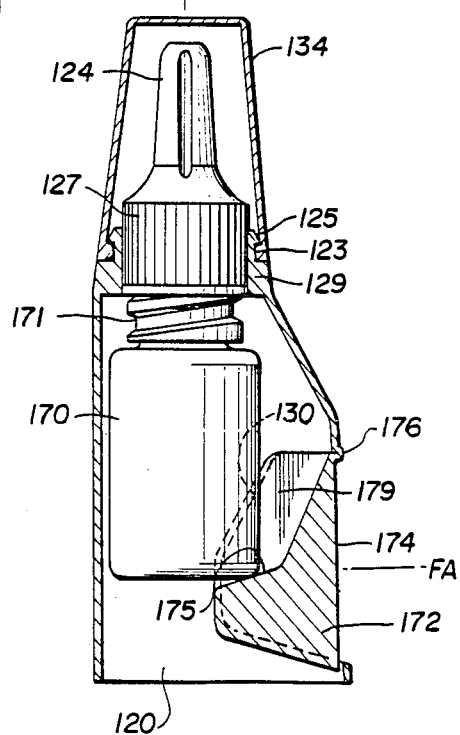
FIG. 8 is a side elevation of the embodiment of FIG. 6 with the cap on and the side wall and cap cut away.

Another embodiment of the present invention is illustrated in FIGS. 6, 7 and 8. For ease of understanding, the embodiment of FIGS. 6, 7 and 8 will have 100 added to the numbers of the embodiment of FIGS. 1 through 5. The hand held metering dispenser 110 includes a housing having front walls 114, back wall 116, and side walls 118 and 120. A top wall 122 has a collar 123 therein through which extends a nozzle 124. The back wall 116 includes an orifice 126, the side wall 118 includes an indenture 128 contiguous with the orifice 126 and the side wall 120 includes an indenture 130 contiguous with the orifice 126. The orifice 126 and the indentures 128 and 130 form substantially a slot. A cap 134 engages and is held on the top wall 122 by a rim 125 on the collar 123.

The nozzle 124 is part of a base 127. The interior of the housing 110 includes a extended portion 129 which engages the circumference of the base 127 of the nozzle 124 and maintains the nozzle mounted to the housing. A container 170 has external threads 171 which are mounted to a pump means similar to that of FIGS. 1 through 5 which is not shown for sake of clarity in FIGS. 6 through 8. The pump means is provided between the container 170 and the nozzle 124 with the base 127 forming part of the pump. The container 170 moves along the coincident pumping and dispensing axis PA and DA, respectively.

The converter or the element which converts the manual force applied along force axis FA through the orifice 126 to move the container 170 along the pumping axis PA is shown in FIGS. 6 through 8 as a hinged element 172 having a generally [L-shaped cross-section as illustrated in FIG. 8 with portions 174 and 175. Portion 174 extends across the orifice 126 and follows the contour of the back wall 116. The portion 175 which is substantially orthogonal to the portion 174 f the converted hinge 172 provides a camming surface which engages the bottom of the container 170. The converter 172 is hinged at 176 to the back wall housing 116 by, for example, a living hinge. Thus, converter 172 is a unitary molded structure with the housing 112. Lateral walls 177 and 179 provide an enclosure around the sides of the container 170 and fill the void of indentures 128 and 130 of the housing.

Although the bottom edge of the converter 172 extends past the orifice 126 and engage the interior of back wall 116 to maintain the converter 172 within the housing, it should be noted that portion 174 may extend exterior the housing back wall 116 without departing from the present invention. The important thing is that it does not extend substantially behind the housing in order to prevent accidental operation of the device during transit. It should also be noted that although pivot 176 is shown as a living hinge and an integral part of the converter 172 and housing 112, the converter 172 may be a separate and distinct element and may be pivotally connected anyplace within the interior of the housing 112. Similarly, tee converter may be hinged at the corner of the L-shape instead of at the ends of one of the legs. It should also be noted that although housing 112 is illustrated as a closed molded device, it may be also formed as a unitary molded device with a living hinge along one of the walls such that it may be opened up to allow insertion of the container 170 other than along the pumping and dispensing axis PA and DA.

The operation of the embodiment of FIGS. 6 though 8 is the same as that of FIGS. 1 through 5 in that a manually applied force along force axis FA onto portion 174 of the converter 172 causes pivotal movement of the converter 172 about pivotal axis 176 to cause surface 175 to apply a force to move the container 170 along the pumping axis PA to actuate the pump to dispense fluid from the container along dispensing axis DA and out through nozzle 124. The hand of the user encompasses the housing 112 and a single finger is used to actuate converter 172. As in the previous embodiment, this minimizes the amount of motion of the housing 112 and the nozzle 124 thereby providing accurate placement of the dispensed fluid.

It is evident from the detailed description of the invention that the objects are attained in that a new and improved metered display dispenser is provided. This dispenser overcomes the problems of the prior art by applying the manual activation force of the metered pump on an axis transverse to the dispensing axis and transverse to the pumping axis. This minimizes lateral displacement of the nozzle. Since the majority of the hand encompasses the housing versus the container and the nozzle is integral to the housing, the lateral motion is minimized. In prior art devices, the hand engages a substantial portion of the container and applied the force in a substantially different direction relative to the dispensing axis and the pumping axis.

Although the invention has been described and illustrated in detail, it is clearly understood that the same is by way of illustration and example only and is not to be taken by way of limitation. The spirit and scope of the present invention is to be limited only by the terms of the appended claims.

What is claimed is:

1. A hand held metered spray dispenser comprising:
   housing means;
   nozzle means extending from the top of said housing means and shaped for insertion into an orifice for directing a spray along a dispensing axis;
   container means movably mounted to the interior of said housing means for holding fluid to be dispensed;
   manual pump means interconnecting said nozzle means and said container means and having a pumping axis substantially coincidental to said dispensing axis for pumping a metered amount of fluid from said container means to said nozzle means in a single pumping cycle;

orifice means in said housing means for providing excess to the interior of said housing means along a manual force axis transverse to said dispensing axis; and converting means pivotally connected to said housing means and engaging said container means for converting a manual force applied through said orifice means along said manual force axis to a force moving said container means along said pumping axis activating said pump means to dispense a metered amount of fluid through said nozzle means wherein said converting means includes hinge means for pivotally mounting said container means to the interior of said housing means with a side of said container means adjacent said orifice means whereby said manual force is applied to said container means through said orifice means.

2. A hand held spray dispenser comprising:
housing means;
dispensing nozzle means on the top of said housing means and having a dispensing axis;
container means for holding a fluid to be dispensed;
means for pivotally mounting said container means to the interior of said housing means;
pump means interconnecting said nozzle means and said container means for pumping a metered amount of fluid from said container means to said nozzle means in a single pumping cycle;
orifice means in said housing means for providing access to said container means from the exterior of said housing means so that a manual force applied to said container means through said orifice means along an axis transverse to said dispensing axis pivots said container means to operate said pumping means to dispense a metered amount of fluid through said nozzle means.

3. A hand held metered spray dispenser according to claim 2 wherein the said container means has a surface juxtaposed said orifice means having a high coefficient of friction.

4. A hand held metered spray dispenser according to wherein said surface includes a plurality of grooves to produce said high coefficient of friction.

5. A hand held spray dispenser according to claim 2 further including a cap means hinged at one side to said housing means for covering said nozzle means.

6. A hand held metered spray dispenser according to claim 5, wherein said housing means, said nozzle means and said cap means are a unitary molded structure.

7. A hand held metered spray dispenser according to claim 2, wherein said pivotal mounting means includes a first portion being unitarily molded with said housing means and a second portion being unitarily molded with said container means.

8. A hand held metered spray dispenser according to claim 2, wherein said pivotal mounting means includes a first portion being unitarily molded with said housing means and a second portion secured to said container means by said pump means.

9. A hand held metered spray dispenser according to claim 2, wherein said pumping means includes return means for returning said pump means and said container means to their initial operating position.

10. A hand held metered spray dispenser according to claim 2, wherein said nozzle means has a substantially conical shape for insertion into a body orifice.

11. A hand held metered spray dispenser according to claim 2, wherein said housing means includes a top wall and four side walls, said nozzle means being in said top wall, said orifice means being in one of said side walls.

12. A hand held metered spray dispenser according to claim 11, wherein two of said side walls each adjacent an opposite edge of said one side wall each include an indenture contiguous with said orifice means in said one side wall to form a slot therewith.

13. A hand held metered spray dispenser according to claim 11, wherein said one side wall is substantially parallel to said dispensing axis and side wall opposed to said side wall is inclined relative to said dispensing axis.

* * * * *

UNITED STATES PATENT AND TRADEMARK OFFICE
CERTIFICATE OF CORRECTION

PATENT NO. : 4,860,738
DATED : August 29, 1989
INVENTOR(S) : Hegemann et al.

It is certified that error appears in the above-identified patent and that said Letters Patent is hereby corrected as shown below:

```
In Col. 4, line 11, "the" should be --The--.
In Col. 5, line 54, delete "[".
In Col. 5, line 58, "f" should be --of--.
In Col. 6, line 12, "tee" should be --the--.
In Col. 7, line 2, "excess" should be --access--.
In Claim 4, line 1, after "to", insert --claim 3--.
In Claim 5, line 1, after "held", insert --metered--.
In Claim 13, line 3, delete second occurance of "to".
In Claim 13, line 4, after said (first occurance) insert
    --one--.
```

Signed and Sealed this

Eleventh Day of September, 1990

Attest:

HARRY F. MANBECK, JR.

*Attesting Officer*    *Commissioner of Patents and Trademarks*